US006897355B2

United States Patent
Trees

(10) Patent No.: US 6,897,355 B2
(45) Date of Patent: May 24, 2005

(54) INTERSPECIFIC *LOBELIA* PLANT

(75) Inventor: Scott Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 236 days.

(21) Appl. No.: 09/817,449

(22) Filed: Mar. 26, 2001

(65) Prior Publication Data

US 2002/0092044 A1 Jul. 11, 2002

Related U.S. Application Data

(60) Provisional application No. 60/192,728, filed on Mar. 27, 2000.

(51) Int. Cl.[7] .............................. A01H 1/00; A01H 1/02
(52) U.S. Cl. ....................................... 800/269; 800/323
(58) Field of Search ................................. 800/323, 269

(56) References Cited

U.S. PATENT DOCUMENTS

PP10,758 P     1/1999 Westhoff

PP12,536 P2 * 4/2002 Trees

OTHER PUBLICATIONS

"Web page" from www.jungpilanzen.hilleride dated Mar. 21, 2000.
"Silverhill Seeds Supplementary Seed Catalogue" Jul. 1996.
Hortus Third A Concise Dictionary of Plants Cultivated in the United States and Canada, MacMillan Publishing Company (1976).
Ball Perennial Manual Propagation and Production, Ball Publishing (1996).
W. Bowden, Canadian Journal of Botany, 60:2054–2070 (1982).

* cited by examiner

*Primary Examiner*—Bruce R. Campell
*Assistant Examiner*—S B. McCormick-Ewoldt
(74) *Attorney, Agent, or Firm*—Wood, Phillips, Katz, Clark & Mortimer

(57) ABSTRACT

This invention relates to a novel interspecific *Lobelia* plant. The *Lobelia* plant of the present invention was developed through a unique interspecific cross between *Lobelia erinus* and *Lobelia valida*.

5 Claims, 2 Drawing Sheets

INTERSPECIFIC *LOBELIA* PLANT

RELATED APPLICATION INFORMATION

This application claims priority from U.S. application Ser. No. 60/192,728, filed on Mar. 27, 2000.

FIELD OF INVENTION

This invention relates to a novel interspecific *Lobelia* plant. The *Lobelia* plant of the present invention was developed through a unique interspecific cross between *Lobelia erinus* and *Lobelia valida*.

This invention also relates to interspecific *Lobelia* seed, interspecific *Lobelia* plants, interspecific *Lobelia* varieties and interspecific *Lobelia* hybrids.

In addition, the present invention also relates to methods for producing interspecific *Lobelia* varieties using *Lobelia erinus* and *Lobelia valida* in breeding as either female or male parents, in order to produce novel types and varieties of interspecific *Lobelia* plants. The present invention also relates to a $F_1$ hybrid or later generation interspecific *Lobelia* plant grown from the interspecific hybrid seed produced by the aforementioned methods.

BACKGROUND OF INVENTION

The genus *Lobelia* includes approximately 375 species of annuals, perennials, shrubs or sometimes trees, native mostly to tropical and warm temperate regions. Irregular tubular flowers and an acrid, milky latex characterizes them. Several herbaceous species are popular in flower gardens and thrive in moist, shady and semi-shady locations. Within the genus, foliage color ranges from light green to bronze green and bronze red and habits from trailing to upright. Flower color ranges from blue, violet, red, yellow or white and is often bicolor (*Hortus Third A Concise Dictionary of Plants Cultivated in the United States and Canada*, MacMillan Publishing Company (1976)).

Cultivated species include: *Lobelia erinus*, a small annual herb, native to southern Africa that bears blue or violet flowers; *Lobelia cardinalis*, a tall, perennial herb commonly called cardinal flower bearing vertical clusters of large, crimson flowers; *Lobelia siphilitica*, the commonly called blue cardinal flower; *Lobelia splendens*, commonly known Mexican *Lobelia*, similar to *Lobelia cardinalis* with the major difference being bronze leaves; and *Lobelia inflata*, known for production of the alkaloid lobeline, used medicinally Id.

Many popular cultivars, including 'Bees Flame' and the Fan Series, have been produced from interspecific hybridization of *Lobelia splendens, Lobelia cardinalis,* or *Lobelia siphilitica.* Collectively these hybrids are known as *Lobelia×hybrida. Lobelia×Gerardii*, a hybrid resulting from a cross between *L.*×'Queen Victoria' and *L. siphilitica*, produces flowers that are often larger than other *Lobelia* species in a range of colors from pink to violet purple (*Ball Perennial Manual Propagation and Production*, Ball Publishing (1996)).

Interspecific hybrids identified as *L.×speciosa* are the result of crossing *Lobelia siphilitica* and *Lobelia cardinalis.* These hybrids whether naturally occurring or artifical show many intermediate morphological characteristics of the two parents. Many tetraploid hybrids of *L.×speciosa* have been produced through intercrossing spontaneous tetraploids and/or those produced using colchicine treatments (W. Bowden. *Canadian Journal of Botany* 60: 2054–2070 (1982)).

SUMMARY OF INVENTION

The present invention relates to an interspecific *Lobelia* plant. The interspecific *Lobelia* plant of the present invention has a pedigree which includes BFP-100 or derivatives thereof.

The present invention also relates to seed, pollen, cuttings and ovules of the interspecific *Lobelia* plant of the present invention. Moreover, the present invention also relates to a tissue culture comprising regenerable cells of the interspecific *Lobelia* plant of the present invention.

Additionally, the present invention relates to interspecific *Lobelia* seed. The seed of the present invention has a pedigree, which includes BFP-100. The present invention also relates to an interspecific *Lobelia* plant produced by growing the seed of the present invention.

The present invention also relates to a *Lobelia* plant having a lineage, which includes *Lobelia* plant, BFP-100 and which exhibits heat tolerance and sky-blue flowers with white centers and initial upright growth followed by a semi-trailing habit.

The present invention also relates to a method for crossing *Lobelia erinus* and *Lobelia valida.* The method involves crossing pollen from a first parent *Lobelia* plant to a second parent *Lobelia* plant and harvesting the resultant first generation ($F_1$) hybrid *Lobelia* seed. The parent *Lobelia* plants used in said method must be a *Lobelia erinus* and *Lobelia valida.* Additionally, the present invention relates to a first generation ($F_1$) hybrid plant produced by growing the hybrid seed produced by said method.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
FIG. 1 shows a photograph of a *Lobelia erinus*×*Lobelia valida* hybrid named BFP-100 of the present invention in a garden location.
Figure 2:
FIG. 2 shows a photograph of *Lobelia erinus*, the female parent, *Lobelia valida*, the male parent, and the *Lobelia erinus*×*Lobelia valida* hybrid named BFP-100 of the present invention.

The interspecific *Lobelia* plant of the present invention was developed through a unique interspecific cross between *Lobelia erinus* and *Lobelia valida*.

This previously unknown interspecific *Lobelia* was discovered as a result of breeding and research efforts which were conducted at Arroyo Grande, Calif. In 1997, a cross was made using *Lobelia erinus* Palace Series Blue With Eye as the female parent (commercially available from Ball Seed Company, 622 Town Road, West Chicago, Ill. 60185). This species exhibits dark purple-blue flowers with white centers or "eyes" and the habit is semi-trailing. The male parent was *Lobelia valida* (purchased from Silverhill Seeds, P.O. Box 53108, Kenilworth, 7745 Cape Town, South Africa). This is an upright species with lavender-blue flowers. In 1997, the resulting $F_1$ seed was collected and germinated. From the flowering progeny, a plant identified as BFP-100 was selected.

Interspecific *Lobelia* plant BFP-100 possesses a number of unique characteristics which are intermediate between the two parents including: sky-blue flowers with white centers or "eyes", initial upright growth followed by a semi-trailing habit, and shape and size of foliage and stems. In addition, the interspecific hybrid is heat tolerant, more vigorous and profusely flowering than either parent.

Selection BFP-100 has not been observed under all possible environmental conditions. The phenotype may vary significantly with variations such as temperature, light intensity and daylength, without, however, any variance in genotype.

The interspecific *Lobelia* plant of the present invention is genetically stable and can be stably reproduced by means of asexual propagation. Cuttings for asexual propagation can be taken at any time of the year and no special hormones or soil mixtures are required. It is expected that any interspecific *Lobelia* can be produced commercially through asexual propagation.

While the interspecific *Lobelia* plant of the present invention is not sterile it maintains low fertility and can thus be employed as a female and/or male parent in traditional breeding. Methods for overcoming interspecific hybrid sterility barriers are known in the art and include, but are not limited to, colchicine treatments, random assertive mating and naturally developing pollen fertility.

The following examples are set forth as representations of specific and preferred embodiments of the present invention. These examples are not to be construed as limiting the scope of the invention in any manner. It should be understood that many variations and modifications can be made while remaining within the spirit and scope of the invention.

EXAMPLE 1

Detailed Description of *Lobelia erinus*×*Lobelia valida* Hybrid Named BFP-100 and Comparison with Cultivar 'Azuro'

The color chart used in the identification of colors described herein is the R.H.S. Colour Chart of The Royal Horticultural Society, London, England. The color values were determined on Mar. 13, 2000 in West Chicago, Ill. The readings were taken between 1:00 p.m. and 1:45 p.m. under approximately 2500 footcandles of light.

The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. 'Azuro' is commercially available from Jungpflanzer-Hiller KG, Kirchheimer Str. 70–74, 73295 Weilheim-Teck, Germany. 'Azuro' is also the subject of U.S. Plant Patent No. 10,758.

| CHARACTERISTIC | NEW VARIETY BFP100 | COMPARISON VARIETY Azuro |
|---|---|---|
| Plant form | Upright to trailing | Upright, mounded |
| Lateral branch diameter | 2 mm | 2 mm |
| Internode length | 3.3 cm | 3–5 cm |
| Stem texture | Smooth | Same |
| Leaf arrangement | Alternate | Same |
| Upper leaf shape | Linear | Same |
| Upper leaf length | 2.7 cm | Same |
| Upper leaf width | .5 cm | .6 cm |
| Upper leaf apex | Rounded | Acute |
| Upper leaf base | Attenuate/sessile | Same |
| Upper leaf margin | Remotely serrate | Same |
| Upper leaf texture | Smooth | Same |
| Upper leaf aspect | Flat | Same |
| Upper leaf color-upper surface | 137A | Same |
| Upper leaf color-lower surface | 137B | 147B |
| Lower leaf shape | Spatulate/obovate | Same |
| Lower leaf length | 5 cm | Same |
| Lower leaf width | 1.3 cm | 1.8 cm |
| Lower leaf apex | Sharply acuminate | Same |
| Lower leaf base | Attenuate/sessile | Same |
| Lower leaf margin | Closely serrate | Same |
| Lower leaf texture | Smooth | Same |
| Lower leaf aspect | Flat | Same |
| Lower leaf color-upper surface | 137B | 137A |
| Lower leaf color-lower surface | 137C | 147B |
| Flowering habit | Continual; 1/axil | Same |
| Flower bud length | 1.1 cm | 1 cm |
| Flower bud shape | Tubular | Same |
| Flower bud diameter | 3 mm | 2 mm |
| Flower shape | Labiate | Tubular |
| Flower Type | 2 lipped | Same |
| Flower diameter | 1.6 cm | 2 cm |
| Flower length | 1.8 cm | Same |
| Flower arrangement | Single/in loose racemes | Same |
| Petal quantity | 5 - 2 upper; 3 lower | Same |
| Upper petal length | 8 mm | 7.5 mm |
| Upper petal width | 3 mm | 5 mm |
| Lower petal length | 1 cm | 5 mm |
| Lower petal width | 6 mm | 2 mm |
| Petal apex | Cuspidate | Same |
| Petal margin | Entire | Same |
| Petal texture | Smooth, dull | Smooth, satiny |
| Flower color | | |
| Upper surface of upper petals | 99C | Between 96B and 96C with spot of close to 89A at base |
| Lower surface of upper petals | 96C | 97A |
| | Lower petals are fused along ½ of their length | |
| Middle lower petal | White from base to outer ⅓. Outer ⅓ (margin) is 99C | Between 96B and 96C |
| Lateral lower petals | White along inner ½ from base to outer ⅓. Outer edge and tip are 99C Yellow spots between 154A & 1A appear at base where petals are joined | Between 96B and 96C |
| Throat color-outside | White with streaks of 96D | White |
| Throat color-inside | White with streaks of 96B | White with spot of 89A |
| Calyx length | 8 mm | 9 mm |
| Calyx diameter | 2 mm | Same |
| Calyx apex | Acuminate | Same |
| Calyx margin | Entire | Same |
| Calyx texture | Smooth | Same |
| Calyx color | 137C | 146A |
| Sepal arrangement | Lower ½ fused | Same |
| Sepal shape | Thin, linear | Same |
| Sepal length | 1.2 cm | 9 mm |
| Sepal width | 1 mm | Same |
| Sepal quantity | 5 | Same |
| Anther length | 2 mm | Same |
| Anther color | 103B | Whitish purple |
| Pistil length | 9 mm | 9 mm |
| Ovary color | 144A | Same |
| Pedicle length | 2 cm | |
| Pedicle diameter | .5 mm | |
| Pedicle color | 141B | 144A |
| Pedicle surface | Smooth | Same |
| Stamen number | 5 | Same |
| Stamen length | 8 mm | |
| Stamen color | 100D | |
| Stigma lobes | 2 | |
| Stigma shape | Round | Same |

| CHARACTERISTIC | NEW VARIETY BFP100 | COMPARISON VARIETY Azuro |
|---|---|---|
| Stigma color | 89A | Purple |
| Style color | 144A | Green |

All references cited herein are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. A method of producing an interspecific *Lobelia* plant, the method comprising the steps of:

a. crossing a *Lobelia erinus* with a *Lobelia valida;* b. recovering the resulting $F_1$ hybrid interspecific *Lobelia* seed;

c. planting the $F_1$ hybrid interspecific *Lobelia* seed and growing into plants; and d. selecting an interspecific *Lobelia* plant.

2. The method of claim 1 wherein the *Lobelia erinus* is the female parent.

3. The method of claim 1 wherein the *Lobelia valida* is the male parent.

4. The method of claim 1 wherein the *Lobelia valida* is the female parent.

5. The method of claim 1 wherein the *Lobelia erinus* is the male parent.

* * * * *